United States Patent
Lichtenberger

(10) Patent No.: US 7,700,651 B2
(45) Date of Patent: Apr. 20, 2010

(54) PREPARATIONS OF PHOSPHOLIPIDS AND PHARMACEUTICALS CONTAINING 5-AMINO SALICYLIC ACID FOR THE TREATMENT OF INFLAMMATORY BOWEL DISEASE

(75) Inventor: Lenard M. Lichtenberger, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 161 days.

(21) Appl. No.: 11/880,059

(22) Filed: Jul. 19, 2007

(65) Prior Publication Data
US 2008/0020056 A1    Jan. 24, 2008

Related U.S. Application Data

(60) Provisional application No. 60/831,843, filed on Jul. 19, 2006.

(51) Int. Cl.
*A61K 31/19* (2006.01)
(52) U.S. Cl. .................................. 514/557
(58) Field of Classification Search ............... 514/557
See application file for complete search history.

(56) References Cited

U.S. PATENT DOCUMENTS

| | | | |
|---|---|---|---|
| 4,918,063 | A | 4/1990 | Lichtenberger |
| 4,950,656 | A | 8/1990 | Lichtenberger |
| 5,032,585 | A | 7/1991 | Lichtenberger |
| 5,043,329 | A | 8/1991 | Lichtenberger |
| 5,763,422 | A | 6/1998 | Lichtenberger |
| 5,955,451 | A | 9/1999 | Lichtenberger |
| 6,638,534 | B1 | 10/2003 | Ishibashi et al. |
| 6,677,319 | B1 | 1/2004 | Stremmel |
| 6,773,720 | B1 | 8/2004 | Villa et al. |

FOREIGN PATENT DOCUMENTS

| | | |
|---|---|---|
| WO | WO 00/76478 A1 | 12/2000 |
| WO | WO 2002/085414 A2 | 10/2002 |
| WO | WO 2005/070465 A2 | 8/2005 |
| WO | WO2005070465 * | 8/2005 |

OTHER PUBLICATIONS

Treed, I., Braun A., Sparla, R., Kuhnel, M., Giese, T., Turner, J.R., Anes, E., Kulaksiz, H., Fullerkrug, J., Stremmel, W., Griffiths, G., Ehehalt, R., "Anti-Inflammatory Effects of Phosphatidylcholine", Sep. 14, 2007, pp. 27155-27164, 282:37, Journal of Biological Chemistry, USA.
Stremmel, W., Merle, U., Zahn, A., Autschbach, F., Hinz, U., Ehehalt, R., "Retarded Release Phosphatidylcholine Benefits Patients with Chronic Active Ulcerative Colitis", Gut 2005;54;966-971 doi:10.1136/gut.2004.052316.
Allgayer, H., et al., A Comparison of Eff. of Sulfa. and its Metabolites on the Metabolism of Endo. vs. Exog. Arachidonic Acid, Immunopharmacology, vol. 15, 1988, pp. 39-46.
Goncalves, E., et al; "Antioxidant Activity of 5-aminosalicylic acid against lipid peroxidation in the presence of vit. C and E", Int. Jour of Phar., vol. 172, 1998:219-228.
Kesisoglou, F., et al; "Liposomal Formulations of Inflam. Bowel Disease Drugs: Local vs. Systemic Drug Delivery in a Rat Model", Pharma. Research, 2005, 22(8): 1320-1330.
Rudolph, M., et al; "A New 5-aminosalicylic acid multi-unit dosage form for the therapy of ulcerative colitis", Euro. Jour. of Pharmaceutics and Biopharma., 2001, 51:183-190.
European Patent Office, International Search Report and Written Opinion, Jun. 2, 2008.

* cited by examiner

*Primary Examiner*—Rei-tsang Shiao
(74) *Attorney, Agent, or Firm*—Jackson Walker L.L.P.

(57) ABSTRACT

A unique composition of a 5-amino salicylic acid (5ASA) and a phospholipid is disclosed for treating Inflammatory Bowel Disease (IBD), where the composition can be a mixture, a molecular association complex or a covalent compound of 5ASA and a reactive phospholipid covalently bonded together via a diazo linkage and to methods for administering the compositions to treat symptoms of IBD.

21 Claims, 15 Drawing Sheets

US 7,700,651 B2

PREPARATIONS OF PHOSPHOLIPIDS AND PHARMACEUTICALS CONTAINING 5-AMINO SALICYLIC ACID FOR THE TREATMENT OF INFLAMMATORY BOWEL DISEASE

RELATED APPLICATIONS

This application claims provisional priority to U.S. Provisional Patent Application 60/831,843 filed Jul. 19, 2006 (19 Jul. 2006), the entire content of which is hereby incorporated by reference.

BACKGROUND OF THE INVENTION

1. Field of the Invention

The present invention relates to unique formulations for treating inflammatory bowel disease (IBD), such as ulcerative colitis, including 5-amino salicylic acid (5ASA) and a phospholipid.

The present invention relates to unique compositions of matter including 5ASA and phospholipid adapted to release 5ASA in a distal small intestine and/or colon, where lesions due to colitis or Inflammatory Bowel Disease (IBD) are present in order to enhance the anti-inflammatory efficacy of 5ASA. In certain embodiment, the phospholipid composition including from about 15 wt. % to about 95 wt. % of phosphatidylcholine (PC) in a bio-compatible carrier and/or resin. The present invention also relates to methods for making and administering the compositions of this invention orally, enterally and/or rectally.

2. Description of the Related Art

For a background of phospholipids and anti-inflammatory pharmaceuticals the reader is directed to U.S. Pat. Nos. 4,918,063; 5,043,329; 4,950,656; 5,032,585; 5,763,422; and 5,955,451 and PCT/US01/51605, incorporated herein by reference.

Inflammatory Bowel Disease (IBD) represents a family of ulcerative diseases including Ulcerative Colitis and Crohn's Disease that affect the colon and distal small bowel. These diseases are manifested by episodes of GI bleeding, diarrhea, fever, infection and in the most advanced cases, GI fistulation are manifested by perforation and cancer. 5ASA has been used medically to manage patients with IBD, though its effectiveness to keep patients in remission has been limited.

Although 5ASA is an effective treatment, there is a need in the art for 5ASA preparations having improved efficacy to treat IBD and to keep patients in remission.

SUMMARY OF THE INVENTION

The present invention provides compositions including a phospholipid (PL) and 5-amino salicylic acid (5ASA).

The present invention also provides compositions including a soy derived phospholipid component and a 5-amino salicylic acid (5ASA) containing component such as Mesalamine, Sulfsalazine, Olsalazine, Balsalazide, or mixtures thereof. The compositions can also include additional components such as a resin (e.g., Eudragrit® S) to facilitate release of the 5ASA-containing component in the distal gut.

The present invention also provides compositions including a soy derived phosphatidylcholine (PC) component and a 5-amino salicylic acid (5ASA) containing component such as Mesalamine, Sulfsalazine, Olsalazine, Balsalazide, or mixtures thereof, where the PC and 5ASA-containing components are surrounded or encapsulated or embedded in a resin (e.g., Eudragrit® S) to facilitate the release the components in the distal gut.

The present invention provides a method for making formulations including a 5ASA component and a phospholipid component.

The present invention also provides a method for making the formulations including a 5ASA and a PC enriched phospholipid component.

The present invention provides methods for administering 5ASA/PL formulations orally, enterally or rectally, where the administration can be a single administration, a periodic administration, an intermittent administration, or administration according to any administration protocol (administration according to a prescribed schedule, e.g., one daily, twice daily, etc.).

The present invention provides methods of treating patients with IBD by administering a composition of this invention directly on a site of IBD injury to reduce inflammation, while: (1) reducing or preventing ulceration of the injury, (2) reducing or preventing further ulceration of the injury, (3) reducing or healing ulceration of the injury, (4) or to maintain an integrity of hydrophobic membranes and/or layers associated with the distal bowels.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
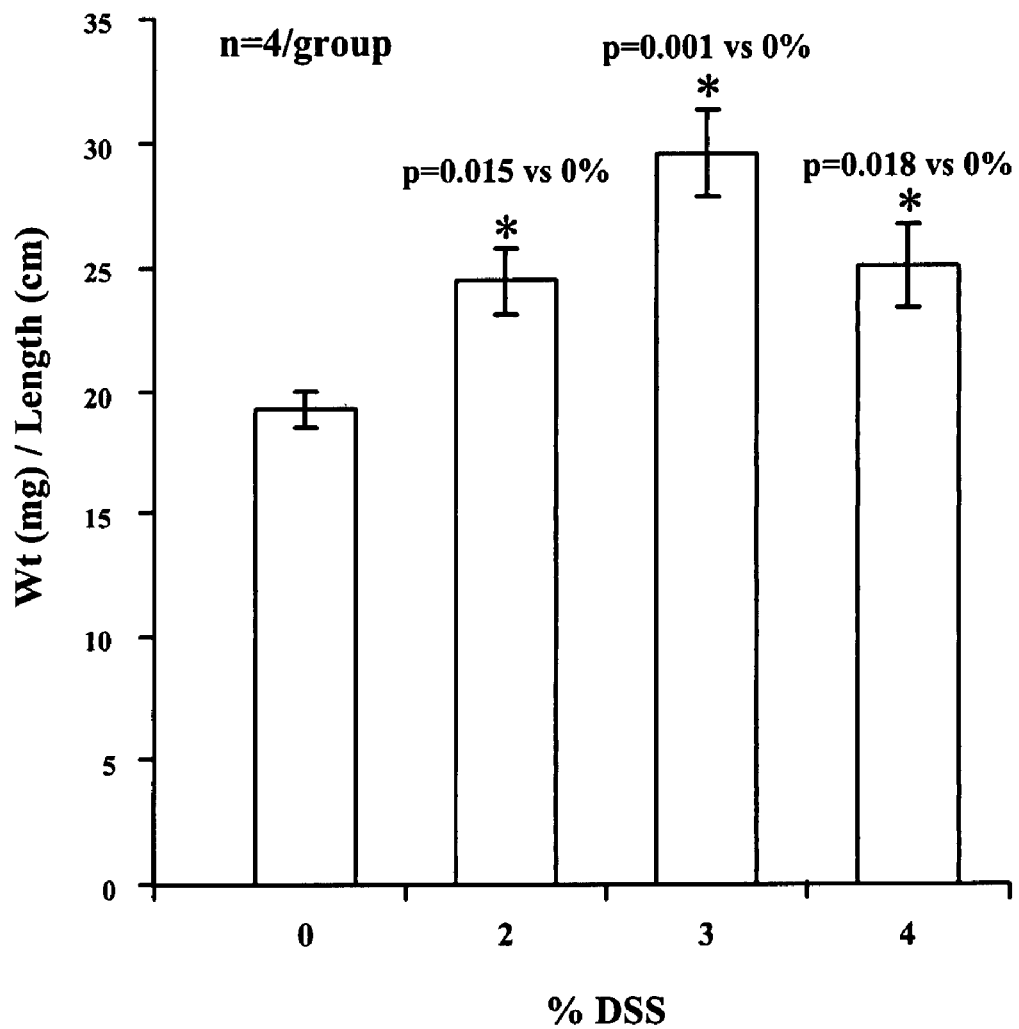
FIG. 1 depicts a graph demonstrating that placing mice on drinking water containing increasing concentrations (0% to 4%) of dextran sodium sulfate (DSS) for 4 days results in increased colonic inflammation as indicated by increased colon tissue weight per unit length.

The inventor has found that compositions of 5-amino salicylic acid (5ASA) and 5ASA based pharmaceuticals and phospholipids have improved activity to reduce colitis in rodent using rodent colitis models. In certain embodiments, the phospholipids are phospholipids derived from soy bean and other sources. In other embodiments, the phospholipids are phospholipids enriched in phosphatidylcholine (PC) or a derivative of phosphatidylcholine. These 5ASA/PC formulations are capable of being administered orally, enterally, or rectally (enema) for treatment or amelioration of GI inflammation, ulceration, bleeding and other symptoms associated with inflammatory bowel disease (IBD), and it's associated sequelae of diarrhea, fever and pain. The compositions of the present invention including 5ASA and a phospholipid enhance anti-inflammatory benefits of the 5ASA and fortify hydrophobic barrier properties of affected mucosa, which are attenuated in IBD.

The invention relates to a method for preparing a composition including a phospholipid, in certain embodiments a phospholipid enriched in phosphatidylcholine (PC), and 5ASA or pharmaceutical formulations including 5ASA for the treatment of IBD. These formulations can be prepared by taking a powder containing 5ASA (e.g., Mesalamine, Sulfsalazine, Olsalazine, Balsalazide, or mixtures thereof) or a larger molecule covalently bound to active 5ASA via a diazo bond and simply mixing it with a phospholipid. In certain embodiments, the 5ASA containing component is simply mixed with an oil-based phospholipid component such as a soy lecithin oil containing PC, e.g., Phosphal 35 SB (P35). Generally, the weight ratio of 5ASA to phospholipid is between about 1:10 and about 10:1. In certain embodiments, the weight ratio is between about 1:5 and about 5:1. In other embodiments, the weight ratio is between about 2:1 and about 1:2. In yet other embodiments, the weight ration is about 1:1.

In some embodiments, the compositions are prepared by heating the components together with mixing to facilitate formulation preparation. An alternative method is to heat the phospholipid and 5ASA to a temperature sufficient for the 5ASA to melt in the phospholipid, generally with good mixing to permit intimate mixing and the formation of associated complexes between 5ASA and phospholipid at the molecular level. The process can be performed in a high temperature solvent or a bio-compatible oil in the absence of air to facilitate the formation of 5ASA/phospholipid associated complexes without oxidative degradation. An alternative method of making the formulation is to make an aqueous formulation including 5ASA and then add the aqueous solution to a vessel coated with a dried lipid film of PC, which will then be vigorous mixed, vortexed, sonicated or subjected to other means of agitation to make a lipidic suspension of the 5ASA/PC. Another method is to dissolve the 5ASA and phospholipid in solvent that dissolves both materials. Mixing the solution with or without heating and then evaporating the solvent. The resulting material can then be ground and encapsulated with a resin for delayed release in the distal gut.

Yet another method of combining 5ASA and a phospholipid (PL) is to covalently bind the molecules together via a diazo bond between the amino group of 5ASA and a reactive phospholipid (PL), e.g., phosphatidylethanolamine (PE), phosphatidylserine or other reactive phospholipids, using standard techniques to make a diazo bond. Similar to the other 5ASA precursors, such as sulfasalazine, osalazine, and basalazide, bacterial enzymes in the colon hydrolyze the diazo bond, liberating the 5ASA and the reactive PL such as PE. The released 5ASA can then cause its intended therapeutic affect, while the released phospholipid helps of maintain or restore the hydrophobic barrier of the affected mucosa of the distal gut, inhibit inflammation and promote healing.

Pre-clinical studies to date show that phospholipids such as PC enhance the efficacy of 5ASA to treat colitis.

Suitable Reagents

Suitable phospholipids for use in this invention include, without limitation, a phospholipid of general formula:

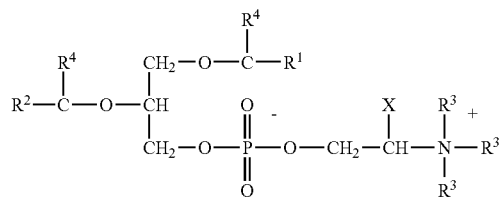

where $R_1$ and $R_2$ are saturated and/or unsaturated substitutions ranging from 8 to 32 carbon atoms, where one or more of the carbon atoms can be replaced by an oxygen atom, a sulfur atom, a nitrogen atom, or other main group element, such as B, C, Si, P, S, Ge, and Ga; $R_3$ is H or $CH_3$, and X is H or COOH; and $R_4$ is =O or $H_2$. Mixtures and combinations of the zwitterionic phospholipids of the general formula.

Examples of zwitterionic phospholipid of formula (II) include, without limitation, phosphatidylcholines such as phosphatidylcholine (PC), dipalmitoylphosphatidylcholine (DPPC), other disaturated phosphatidylcholines or unsaturated phosphatidylcholines, phosphatidylethanolamines, phosphatidylinositol, phosphatidyl serines sphingomyelin or other ceramides, or various other zwitterionic phospholipids, phospholipid containing oils such as marine and/or fish oils enriched in Omega-3 fatty acids, lecithin oils derived from soy beans, dimyristoyl phosphatidylcholine, distearoylphosphatidylcholine, dilinoleoylphosphatidylcholine (DLL-PC), dipalmitoylphosphatidylcholine (DPPC), soy phophatidylchloine (Soy-PC or $PC_S$) and egg phosphatidycholine (Egg-PC or $PC_E$). In DPPC, a saturated phospholipid, the saturated aliphatic substitution $R_1$ and $R_2$ are $CH_3$—$(CH_2)_{14}$, $R_3$ is $CH_3$ and X is H. In DLL-PC, an unsaturated phospholipid, $R_1$ and $R_2$ are $CH_3$—$(CH_2)_4$—CH=CH—$CH_2$—CH=CH—$(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid). In Soy-PC, which in addition to the saturated phospholipids (palmitic acid and stearic acid) is a mixture of unsaturated phospholipids, (oleic acid, linoleic acid and linolenic acid). In PC derived from marine animals (e.g. krill, salmon) the $R_1$ and $R_2$ groups may constitute the Omega-3 fatty acids: eicosapentaenoic acid (EPA) and docosahexaenic acid (DHA). The preferred zwitterionic phospholipid include, without limitation, dipalmitoyl phosphatidylcholine, phosphatidyl choline, or a mixture thereof.

EXAMPLES

Preparation of Compositions

Phosal 35 SB, a soy lecithin oil containing approximately 35 wt. % phosphatidylcholine (PC), was placed in glass beaker to which 5ASA (or a 5ASA containing pharmaceutical) was added under moderate heat, about 40° C., and stirring until a 1:1 weight ratio was attained. The resulting oil-based formulation was coated with a pH-sensitive polymer, e.g., MultiSal™, or Eudragrit®-S, to form polymer encapsulated micro-spheres of the 5ASA/PC composition. These encapsulated micro-spheres are formed so that the 5ASA and PC are released only when the drug reaches the distal gut, where the pH is 7 or above and the polymer coating degrades. This formulation was then added to the diet of mice or rats for evaluation. The mice or rats were placed on 3% dextran sodium sulfate (DSS) solution included in their drinking water to induce colitis.

An alternative method to the oil-based formulation described above is to suspend 5ASA or a 5ASA containing pharmaceutical in water or an appropriate aqueous solution. The aqueous solution is then added to a second container coated with a dried lipid film of PC. The resulting mixture is then subjected to vigorous mixing, vortexing, sonication or other means of agitation to form an aqueous lipidic suspension for oral, enteral or rectal (enema) administration.

The term "bio-compatible oil" means any oil that has been approved for human consumption by the FDA or animal consumption. The bio-compatible oil or oil mixture can either naturally include a phospholipid or has had a phospholipid added thereto.

Suitable bio-compatible oils include, without limitation, any oil approved for human or animal consumption by the FDA including natural oils such as plant or animal oils or their derivatives or synthetic oils and especially natural oil that are rich in phospholipids such as lecithin oils from soy beans. Exemplary examples of such oils include, essential oils, vegetable oils and hydrogenated vegetable oils, animal oils such as peanut oil, canola oil, avocado oil, safflower oil, olive oil, corn oil, soy bean oil, sesame oil, vitamin A, vitamin D, vitamin E, fish oils, or the like.

Examples using C57BL/6 Mice in a Rodent Colitis Model

Groups of four C57BL/6 mice were exposed to differing amount of dextran sodium sulfate (DSS) in their drinking water for a four day period of time. The mice were then euthanized and colon tissue weight per length measurements for each group of mice were made. Referring now to FIG. 1, DSS treatment resulted in colonic inflammation or edema as measured by increased colon tissue weight per length, where 3% DSS was shown to cause the greatest increase in the weight to length measurement.

Figure 2:
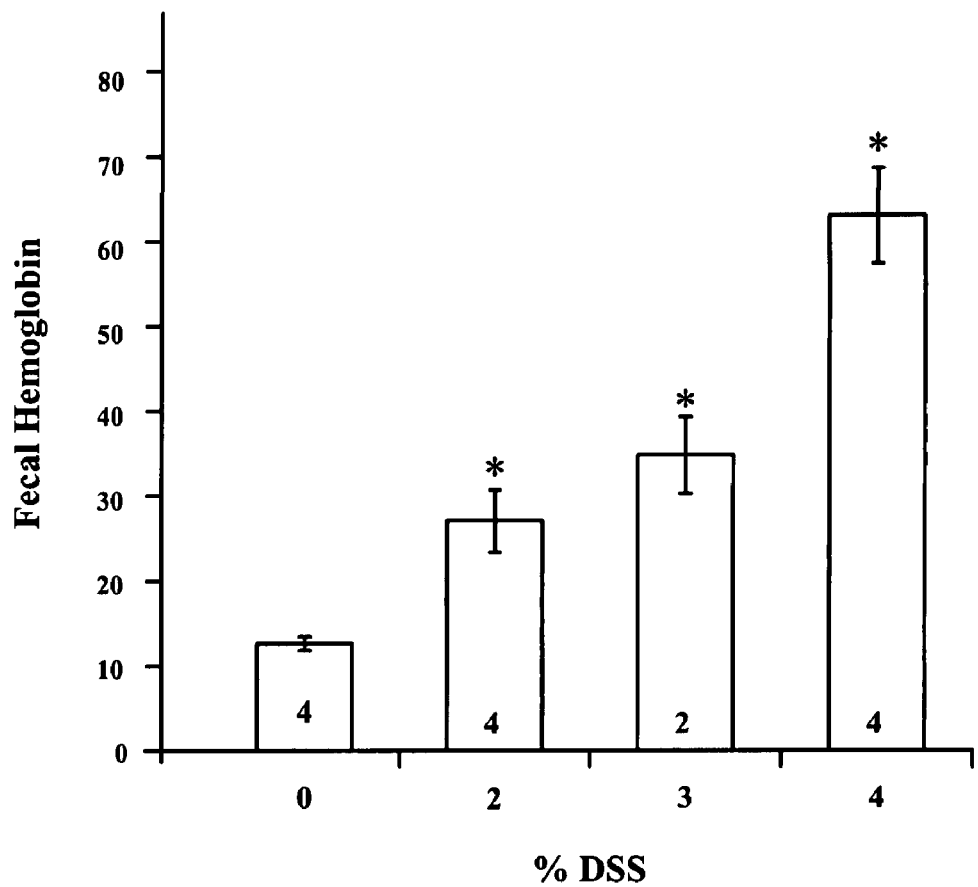
FIG. 2 depicts that increasing concentrations of DSS in the drinking water over a 4 day period induces a dose-dependent increase in GI bleeding of mice as measured by fecal hemoglobin concentration.

Groups of C57BL/6 mice were exposed to differing amount of dextran sodium sulfate (DSS) in their drinking water for a four day period of time. The mice fecal hemoglobin measurements were made at the end of the four day period. Referring now to FIG. 2, DSS treatment resulted in increased fecal hemoglobin with increasing concentration of DSS in their drinking, with 4% DSS showing the highest fecal hemoglobin.

Figure 3:
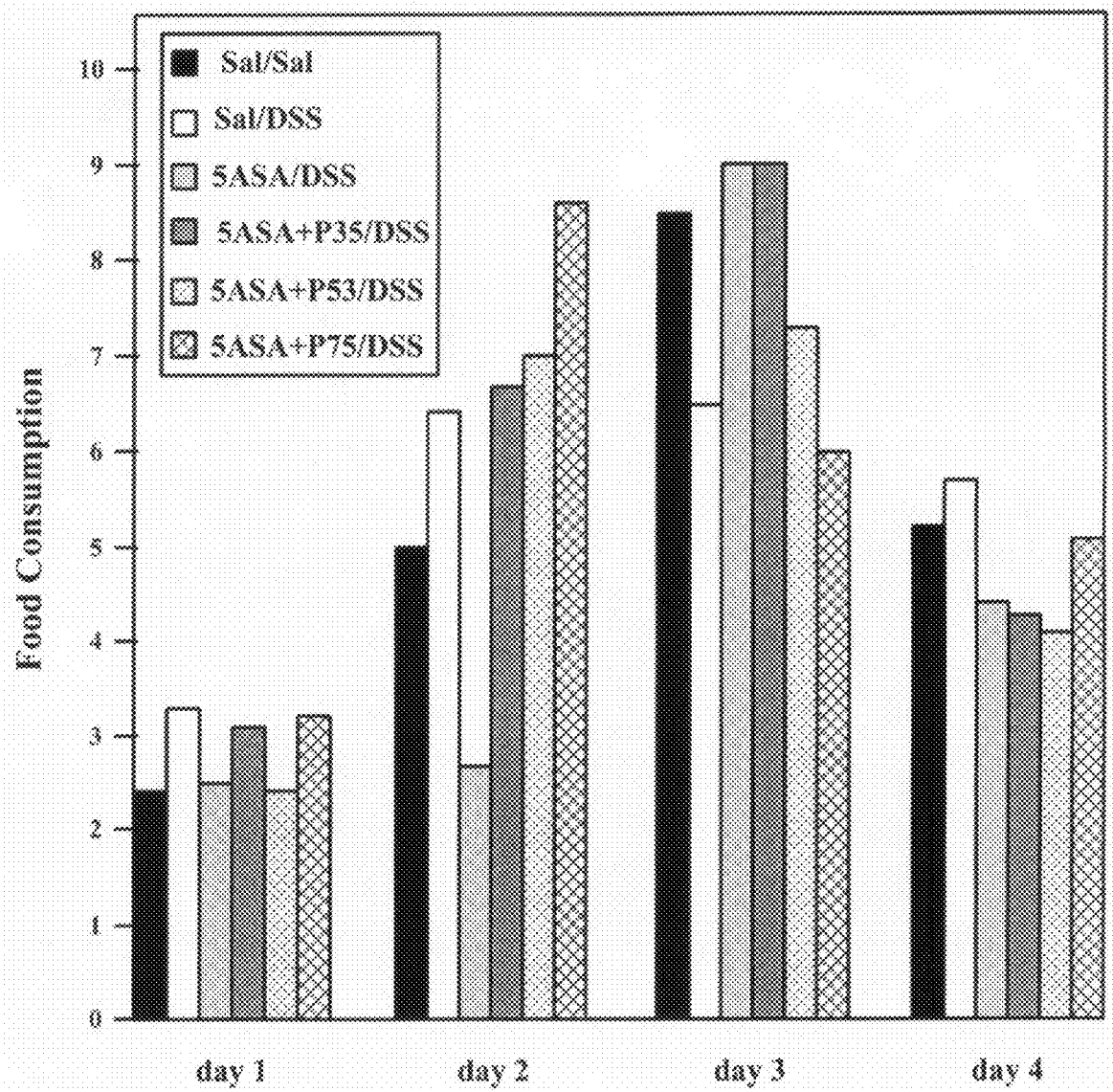
FIG. 3 demonstrates the food consumption of mice eating diets containing 5ASA alone (100 mg/kg body weight) or 5ASA in combination on a 1:1 weight basis with three different soy PC preparations, P35, P53 or P75, containing 35%, 53% or 75% PC, respectively. All but one group labeled Sal/Sal had access to drinking water containing 3% DSS to induce colitis.

Groups of C57BL/6 mice were exposed to different diets and their daily food consumption (grams/day) were measured over a four day period of time. Group 1 represented the control group receiving saline without DSS and regular food without any 5ASA containing formulation. Group 2 represented a DSS control receiving saline with 3% DSS and regular food without any 5ASA containing formulation. Group 3 represented a 5ASA treated group receiving saline containing 3% DSS and a diet including 5ASA MultiSal™ encapsulated micro-spheres. Groups 4 through 6 are designed to compare 5ASA to three oil-based 5ASA/PC formulations. Group 4 represented a 5ASA/P35 (a 1:1 weight ratio of 5ASA and Phosphal® 35SB, an oil-based soy lecithin product containing about 35 wt. % PC) treated group receiving saline containing 3% DSS and a diet including 5ASA/P35 MultiSal™ encapsulated micro-spheres. Group 5 represented a 5ASA/P35 (a 1:1 weight ratio of 5ASA and Phosal® 53 MCT, an oil-based soy lecithin product containing about 53 wt. % PC) treated group receiving saline containing 3% DSS and a diet including 5ASA/P53 MultiSal™ encapsulated micro-spheres. Group 6 represented a 5ASA/P35 (a 1:1 weight ratio of 5ASA and Phosal® 75 SA, an oil-based soy lecithin product containing about 75 wt. % PC) treated group receiving saline containing 3% DSS and a diet including 5ASA/P75 MultiSal™ encapsulated micro-spheres. Referring now to FIG. 3, the food consumption (grams/day) of mice placed on the diets described above. The first three bars evidence feeding patterns of normal mice in the absence and presence of 5ASA in the feed, while the last three bars represent the feeding patterns of mice in the presence of the 5ASA/PC formulations. FIG. 3 indicates that the active materials did not significantly affect the eating patterns of the mice.

Mouse Data Comparing 5ASA and 5ASA:PL Formulations on Treating Induced Colitis

Figure 4:
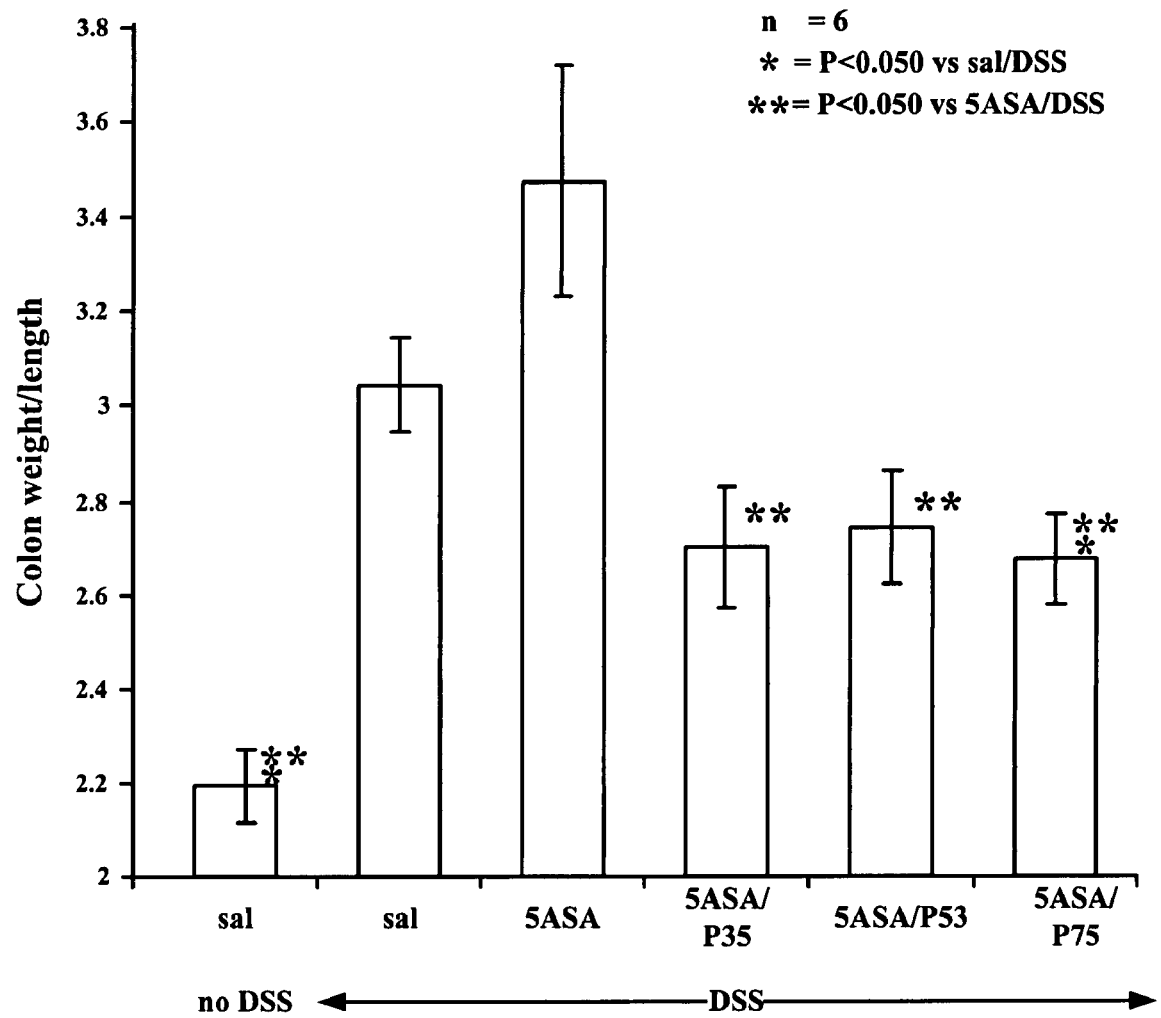
FIG. 4 demonstrates changes in colonic inflammation, as indicated by increased colon tissue weight per unit length in mice fed the experimental diets and placed on 3% DSS in the drinking water to induce colitis.

The previous examples show that drinking water comprising saline containing 3% dextran sodium sulfate (DSS) is capable of inducing a colitis type disorder in mice. Now, the 5ASA:PL formulations can be compared to 5ASA in treating the colitis type disorder in mice. Groups of mice were placed on drinking water comprising saline containing 3% DSS for four days to induce a colitis type disorder and then treated with the compositions of this invention. The efficacy of the treating compositions were determined by measuring colon tissue weight per length. Referring now to FIG. 4, colonic inflammation as measured by an increased colon tissue weight per given length showed partial reversal when treated with saline, 5ASA, 5ASA:P35, 5ASA:P53 and 5ASA:P75 combined with DSS and administered to the mice in their diet with a group of non-DSS treated mice and normal diet. The data showed that the three 5ASA:PL formations are superior to 5ASA alone in reversing tissue inflammation as measured by an increased colon tissue weight to length.

Figure 5:
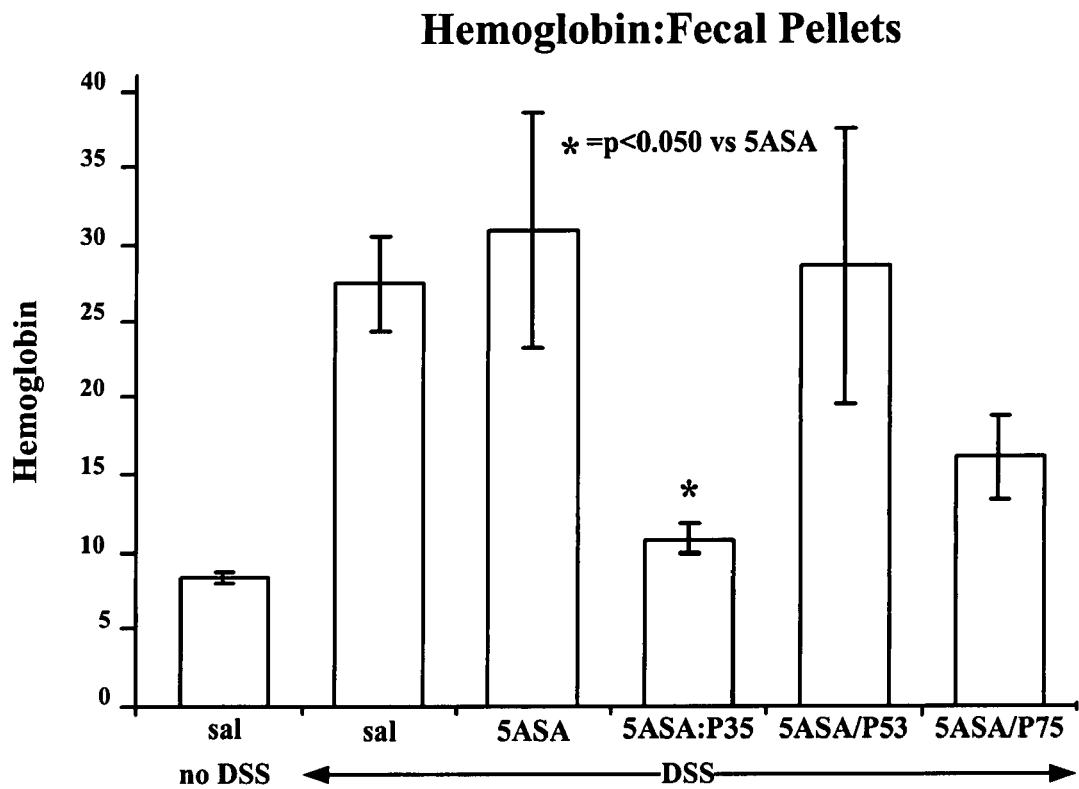
FIG. 5 demonstrates changes in fecal blood loss in mice fed the experimental diets and placed on 3% DSS in the drinking water to induce colitis.

Groups of mice were placed on drinking water comprising saline containing 3% DSS for four days to induce a colitis type disorder and then treated with the compositions of this invention. The appearance of blood as indicated by an increased hemoglobin content in the feces was measured to determine the efficacy of 5ASA versus the 5ASA:PL formulations. Referring now to FIG. 5, hemoglobin content in mice feces was significantly reduced for the mice placed on a diet containing the 5ASA:P35 formulation and 5ASA:P75 compared to saline/DSS and 5ASA/DSS.

Figure 6:
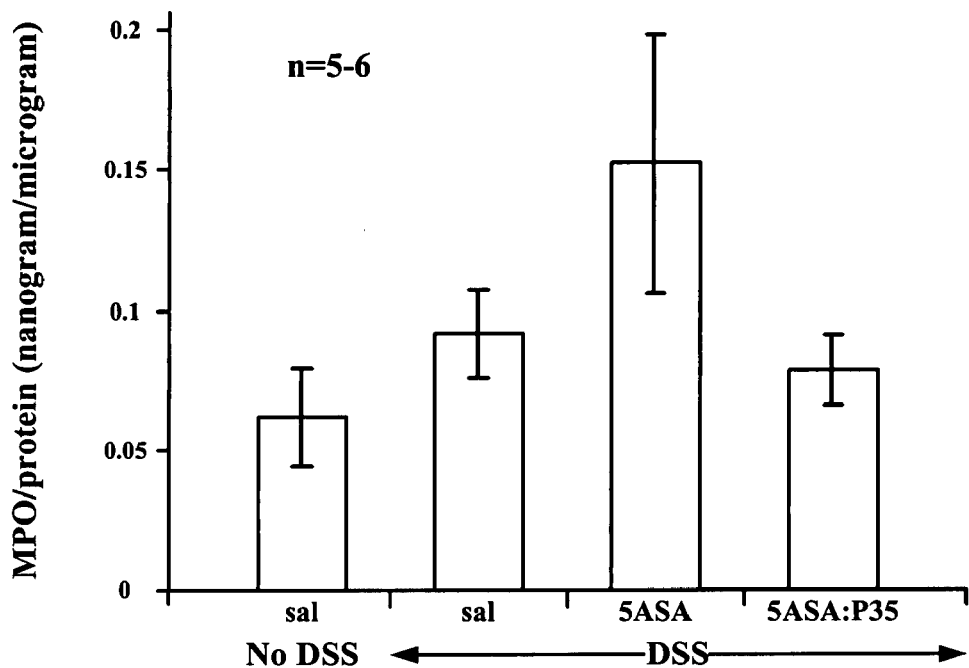
FIG. 6 demonstrates changes in colonic myeloperoxidase (MPO) in mice fed the experimental diets and placed on 3% DSS in the drinking water to induce colitis.

Groups of mice were placed on drinking water comprising saline containing 3% DSS for four days to induce a colitis type disorder and then treated with the compositions of this invention. Colonic inflammation as indicated by an increased tissue myeloperoxidase (MPO) activity was measured to determine the efficacy of saline, 5ASA and 5ASA:PC35. Referring now to FIG. 6, colonic inflammation was reduced for the mice placed on diets containing the 5ASA:P35 formulation.

Figure 7:
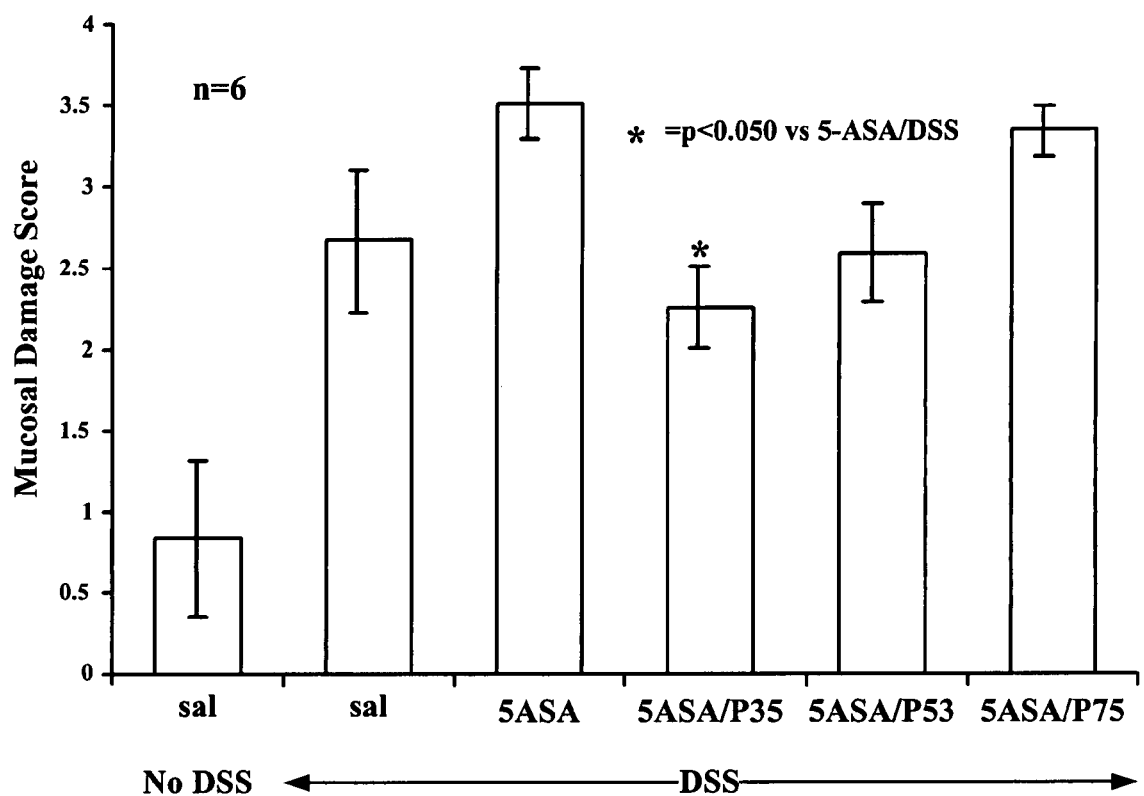
FIG. 7 demonstrates changes in colonic mucosal histology, using a score from 0 (normal) to 4 (complete absence of mucosal glandular structure) in mice fed the experimental diets and placed on 3% DSS in the drinking water to induce colitis.

Groups of mice were placed on drinking water comprising saline containing 3% DSS for four days to induce a colitis type disorder and then treated with the compositions of this invention. Colonic mucosa were viewed through a light microscope and histologically scored using a scoring system, where 0 represents normal colonic mucosa and 4 represent a total loss of colonic glandular structure. Referring now to FIG. 7, the 5ASA/P35 formulation significantly reduced microscopic injury to the colonic mucosa in mice placed on a diet containing 5ASA:P35.

The rodent data clearly shows a positive enhancement of the efficacy of 5ASA in the distal gut when the administered formulation includes a phospholipid.

Rat Data Comparing 5ASA and 5ASA:PL Formulations on Treating Induced Colitis

Rats were placed on drinking water containing 4% dextran sodium sulfate (DSS) for 5 days and 20 hours to induce colitis after which they were returned to normal drinking water. The animals were then intragastrically administered twice daily for 6 subsequent days with: (a) saline (DSS control); (b) 5ASA at a dose of 100 mg/kg; (c) a 1:1 wt. ratio of 5ASA and Phosal 35 SB (an oil-based formulation); or (d) a 1:2 wt. ratio of 5ASA and Phospholipon 90G (an aqueous lipidic suspension) at the same dose of 5ASA, 100 mg/kg, b.i.d. The formulations (c) and (d) are phosphatidylcholine (PC) associated 5ASA formulations, where the PC and 5ASA are associated at the molecular level. These treatments are designed to compare the efficacy of 5ASA and two different PC:5ASA formulations.

At 1, 3 and 6 days, rats were euthanized and colonic tissue, blood and fecal matter were collected for biochemical and histological analyses to assess colonic inflammation and GI bleeding. A separate group of rats were not placed on DSS and served as "normal controls."

Figure 8:
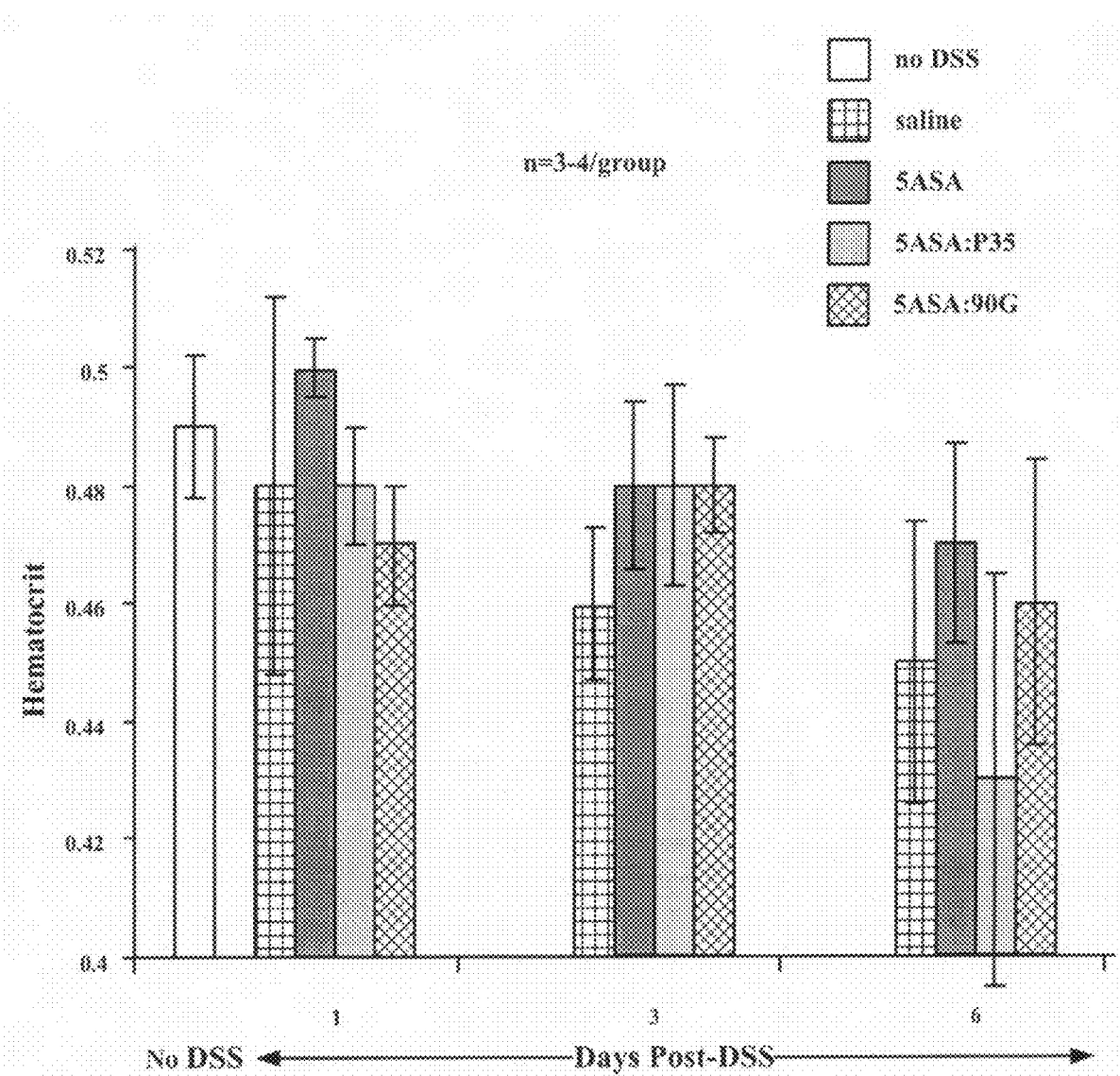
FIG. 8 depicts changes in hematocrit levels in Sprague Dawley male rats during a 6 day recovery period after DSS induced colitis for saline, 5ASA and two PC:5ASA formulations.

Referring now to FIG. 8, changes in hematocrit during the 6 day recovery period were measured from the euthanized rats. Changes in hematocrit levels represent an indirect estimate of anemia and internal (GI) bleeding among the groups over the 6 day recovery period. It can be appreciated that although a modest <10% decrease in the hematocrit levels were seen in all the groups post DSS exposure as compared to the no DSS or "normal control" hematocrit levels, there were no significant differences in this parameter among the test groups over the 6 day recovery period.

Figure 9:
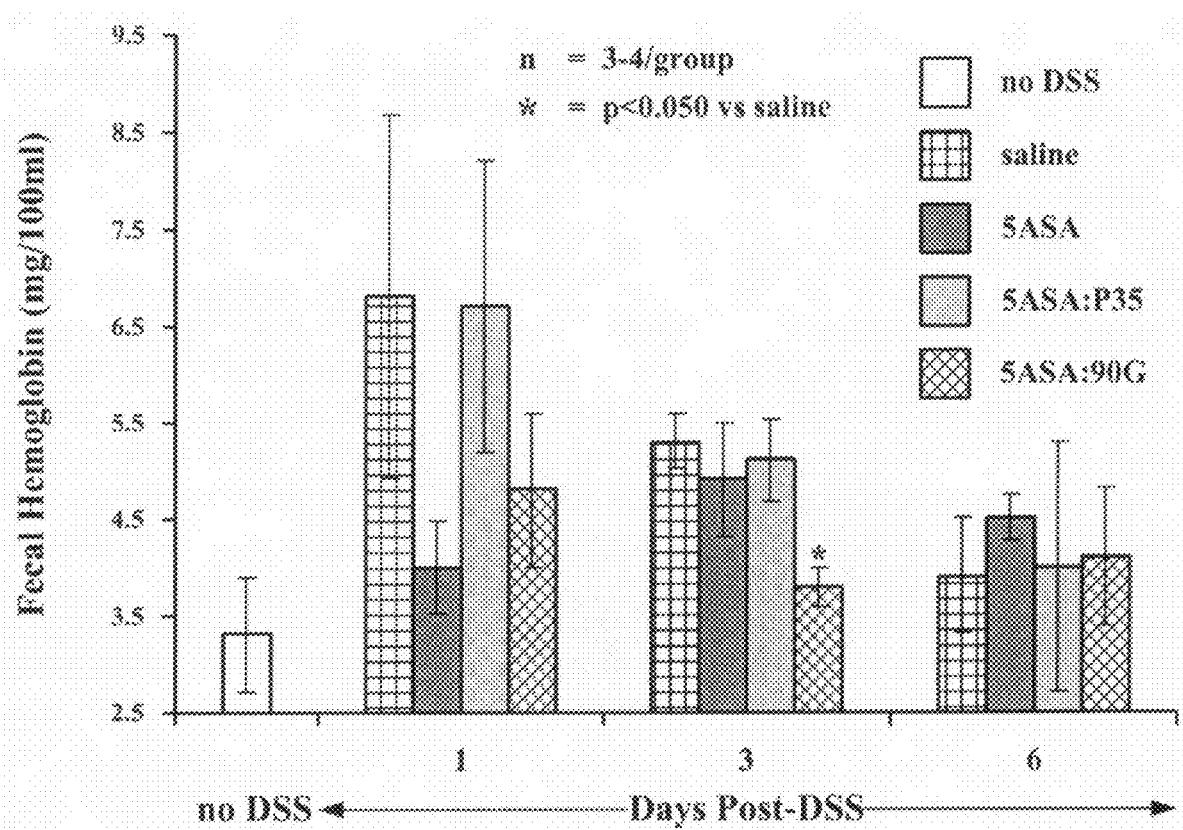
FIG. 9 depicts changes in fecal blood loss in Sprague Dawley male rats during the 6 day recovery period after DSS induced colitis for saline, 5ASA and two PC:5ASA formulations.

The changes in fecal hemoglobin are shown in FIG. 9. In can be seen that fecal blood was detected during the first day of the recovery period in most of the test groups (vs normal control values) with a suggestion that 5ASA±90G may have had a beneficial effect in reducing fecal blood loss.

Figure 10:
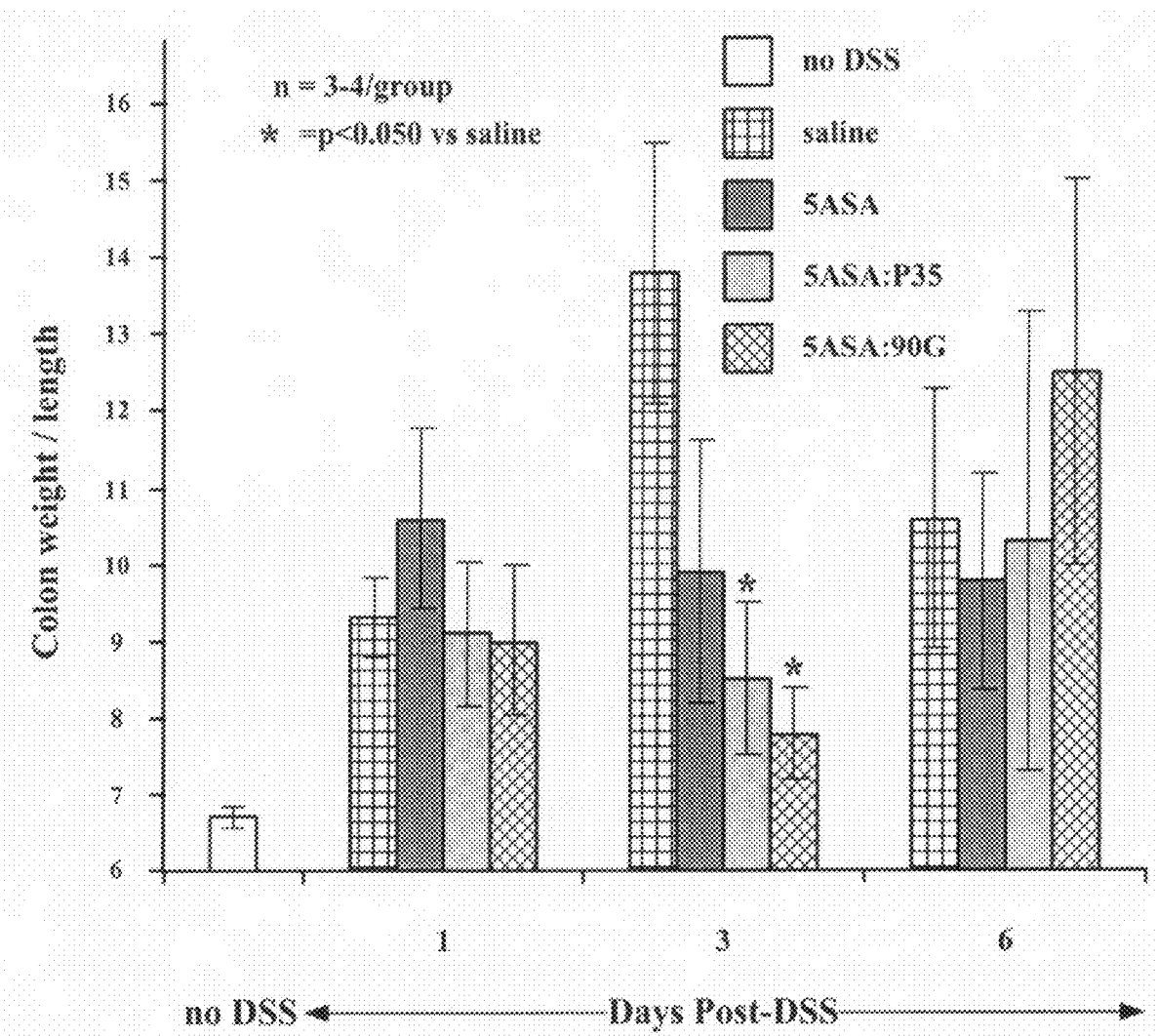
FIG. 10 depicts changes in colonic tissue edema in Sprague Dawley male rats during the 6 day recovery period after DSS induced colitis for saline, 5ASA and two PC:5ASA formulations.

Colonic inflammation and injury were assessed by measuring a number of biochemical and histological indices. First, tissue edema were assessed by measuring tissue wet weight/unit length. These results which are presented in FIG. 10, demonstrate that intestinal edema was maximal 3 days post-DSS in saline-treated controls, and this inflammatory change was reduced by 5ASA (non significantly), and further decreased (significantly) in rats treated with the two PC-[5ASA] formulations. There were no significant differences among the groups in this parameter 6 days post-DSS, with some indication that the animals treated with 5ASA in combination with 90G had a rebound episode of inflammation.

Figure 11:
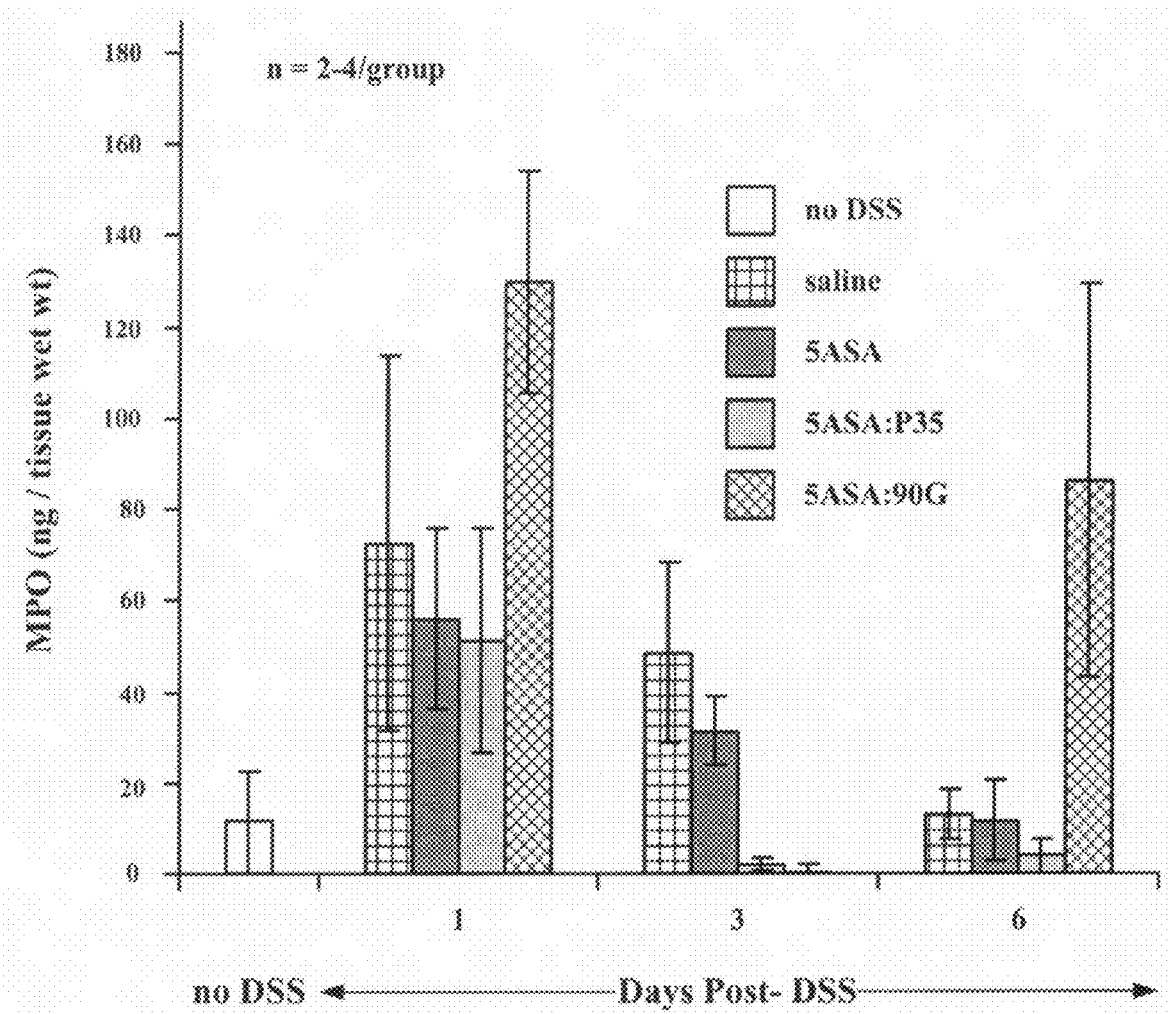
FIG. 11 depicts changes in colonic MPO activity in Sprague Dawley male rats during the 6 day recovery period after DSS induced colitis for saline, 5ASA and two PC:5ASA formulations.

Colonic myeloperoxidase (MPO) activity, a biochemical marker of neutrophil infiltration into the tissue, was measured as another marker of inflammation. The results presented in FIG. 11 demonstrate similar, but more dramatic changes to those described above, with 5ASA showing a reduction on day 3 and both PC-[5ASA] formulations further decreasing MPO activity to almost undetectable levels. MPO activity returned to normal control levels by 6 days in all groups, except for the group treated with 5ASA in combination with 90G.

Figure 12:
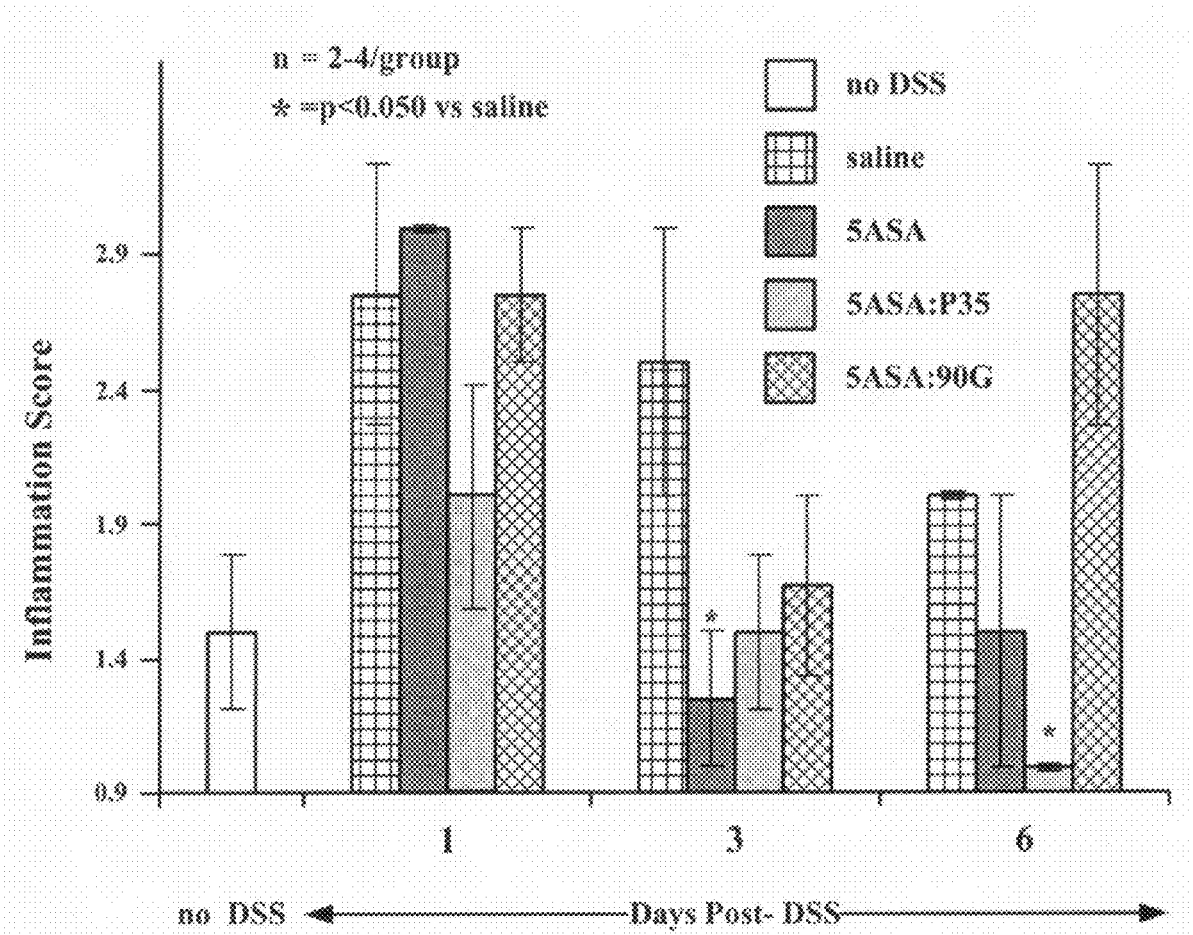
FIG. 12 depicts changes in the number of inflammatory cells in lamina propia of colonic submucosa in Sprague Dawley male rats during the 6 day recovery period after DSS induced colitis for saline, 5ASA and two PC:5ASA formulations.

Tissue histology was scored (under blinded conditions) for signs of injury and inflammation. To assess inflammation we scored the number of inflammatory cells in the lamina propia of the colonic submucosa using a scoring system from 1 (normal) to 4 (highly inflamed). These results, shown in FIG. 12, demonstrate that 5ASA-treated rats had a reduced number of inflammatory cells with the 5ASA/P35 showing comparable or superior anti-inflammatory activity at 3 and 6 days and again 90G in combination with 5ASA causing a rebound of inflammation at 6 days.

Figure 13:
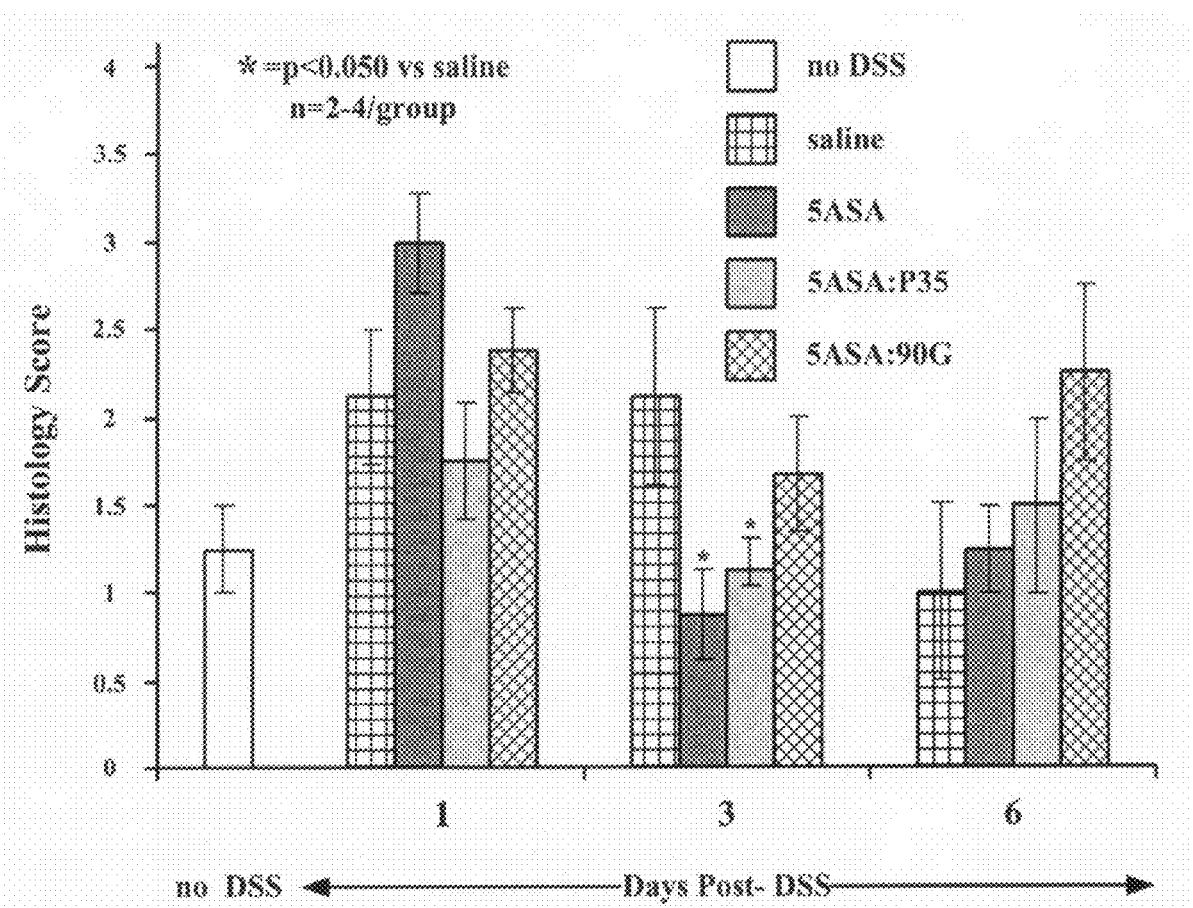
FIG. 13 depicts changes in colonic mucosal injury in Sprague Dawley male rats as assessed histologically during the 6 day recovery period after DSS induced colitis for saline, 5ASA and two PC:5ASA formulations.

To assess colonic mucosal injury, a histological scoring system was used, where: 0=normal mucosa; 1=surface injury; 2=injury extending into the mid glandular region; 3=injury extending into the deep glandular region; and 4=injury extending into the serosal (muscle) layer. FIG. 13 shows that mucosal injury was increased in all groups day 1 post-DSS, and by day 3 there was a recovery in rats treated with 5ASA±PC with the 5ASA/P35 showing more consistent evidence of mucosal protection than 90G.

Conclusions

The protocol used in the above series of experiments, proves to be a very useful rodent model system to evaluate the therapeutic efficacy of 5ASA and PC-5ASA formulations to accelerate the recovery of experimentally (DSS)-induced colitis. Interestingly, it appears that inflammation progresses for the first 3 days after withdrawal from DSS, the colitis inducing agent, and subsides by day 6. Using a number of biochemical and histological markers, it appears that 5ASA at a dose of 100 mg/kg significantly reduces colonic inflammation and tissue injury 3 days post-DSS in comparison to saline-treated control values. The oil-based 5ASA/P35SB formulation showed a further improvement in the recovery from colitis (vs 5ASA alone) in 2 out of 4 markers of inflammation. In contrast, the 5ASA/90G formulation had a biphasic effect with a rebound of inflammation occurring 6 days post-DSS. It is our recommendation that this recovery experiment, using the above model system, be repeated using a lower less effective dose of 5ASA (50 mg/kg b.i.d.), and that we focus our efforts on the oil-based 5ASA/P35 formulation, to determine if a more clear and convincing enhancement in the anti-inflammatory efficacy of our PC-5ASA test formulation can be demonstrated in comparison to 5ASA alone.

Rat Data Comparing 5ASA and 5ASA:PL Formulations on Treating Induced Colitis

The following experiments were designed to compare the efficacy of 5ASA versus 5ASA:PC formulations in treating rats that had been subjected to colitis induced by adding 4% dextran sodium sulfate (DSS) to their drinking water for over 5 days (5 day, 20 hours) and then returned to normal drinking water. The rats were then treated with 5ASA, in this experiment at a lower dose (50 mg/kg, BID) than that previously studied, in the absence or presence to a PL component for 3 days post DSS induced colitis.

Thirty two healthy male rats used in the study. Rats comparable with respect to protocol, supplier, sex, and weight were divided serially into 4 groups. Group 1 were given drinking water without added DSS. Groups 2-4 received drinking water containing 4% DSS for 6 days. At day 6, Group 2 received 1 mL saline BID intra gastrically. Group 3 received 5ASA (50 mg/Kg) BID intra gastrically. Group 4 received 5ASA (50 mg/Kg):Phosal 35SB:MCT oil (1:1:0.3), referred to heretofore as 5ASA:PC BID intra gastrically, where MCT=Medium Chain Triglyceride.

At day 9, the rats were euthanized and the following were measured: (a) hematocrit, (b) fecal hemoglobin, (c) colon weight/length, (d) colon myeloperoxidase (MPO), (e) colonic surface hydrophobicity and (f) colon histology.

In this study, rats were placed on regular drinking water (Group 1) or water containing 4% DSS and then intragastrically administered: saline (Group 2); 5ASA (Group 3) at a dose of 50 mg/kg BID); or 5ASA:PC (P35SB at 1:1 wt ratio) (Group 4) for 3 days at which time the following changes were seen.

Figure 14:
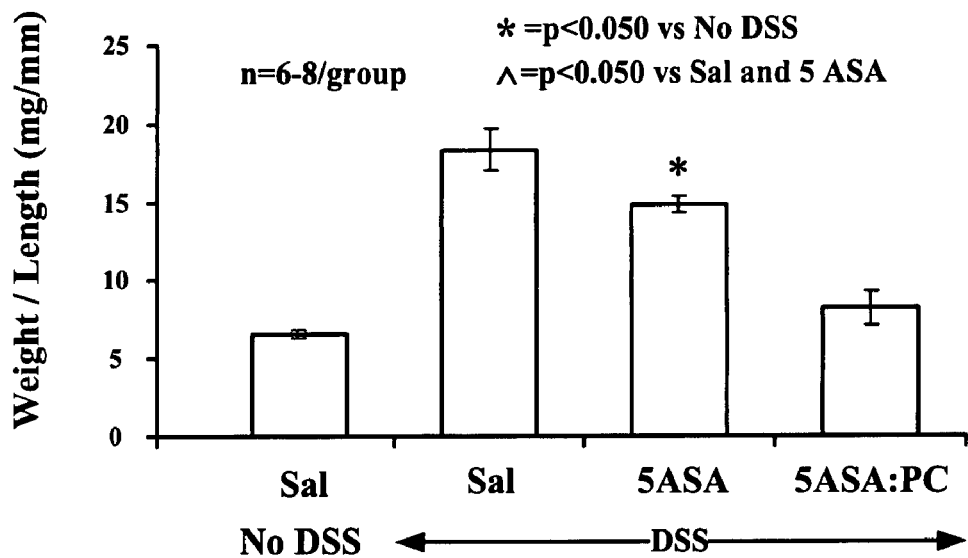
FIG. 14 demonstrates changes in colon tissue weight per unit length in Sprague Dawley male rats during a recovery period after DSS induced colitis for saline with no DSS in the drinking water and saline, 5ASA and a PC:5ASA formulation with DSS in the drinking water.

Referring now to FIG. 14, the colon weight/length data is shown. This measure of mucosal edema demonstrated a significant increase when comparing the DSS saline-treated group (Group 2) with the absolute control (no DSS, Group 1). This DSS-induced mucosal edema was partially reversed by 5ASA at a dose of 50 mg/kg BID (Group 3), and completely reversed in the 5ASA:PC group (Group 4), with significant differences observed between the rats of Group 4 versus the rats of Groups 2 & 3, but not the rats of Group 1.

Figure 15:
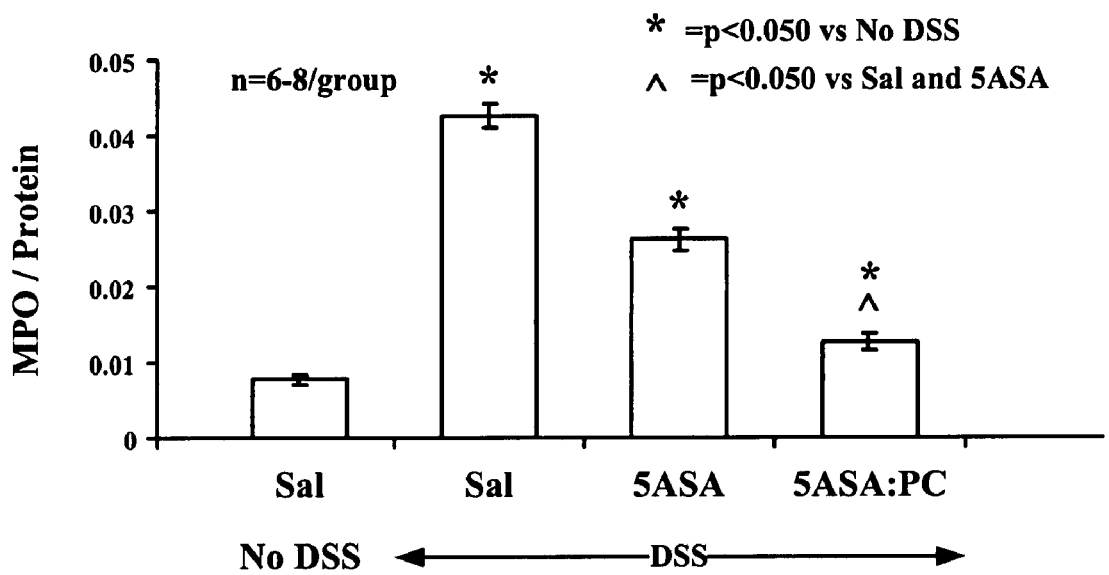
FIG. 15 depicts changes in colonic MPO activity in Sprague Dawley male rats during a recovery period after DSS induced colitis for saline with no DSS in the drinking water and saline, 5ASA and a PC:5ASA formulation with DSS in the drinking water.

Referring now to FIG. 15, the MPO Protein data is shown. This biochemical measure of inflammation showed the same pattern as outlined above, with DSS inducing a significant increase in MPO activity versus the control Group 1 (no DSS), and this inflammation was partially and completely reversed by 5ASA and 5ASA:PC, respectively. Significant differences ($p<0.05$) were observed between the rats of Group 4 versus the rats of Groups 2 & 3, but not the rats of Group 1.

Figure 16:
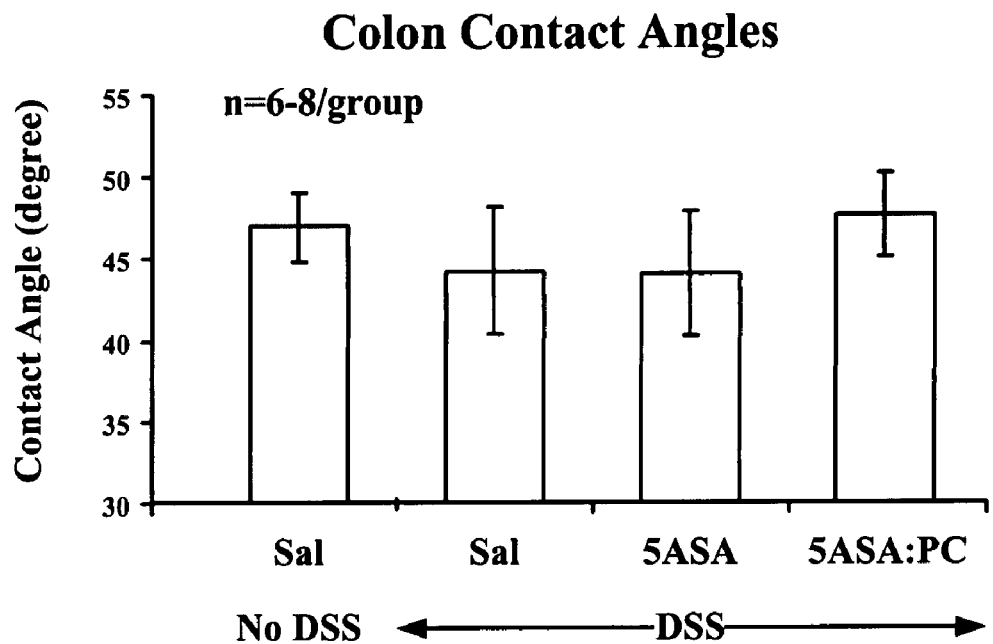
FIG. 16 depicts changes in colon contact angles in Sprague Dawley male rats during a recovery period after DSS induced colitis for saline with no DSS in the drinking water and saline, 5ASA and a PC:5ASA formulation with DSS in the drinking water.

Referring now to FIG. 16, colon contact angle analysis data is shown. No differences in colonic mucosal surface hydrophobicity was observed between groups, possibly because this surface property had recovered fully by 3 days post-DSS induced colitis.

Figure 17:
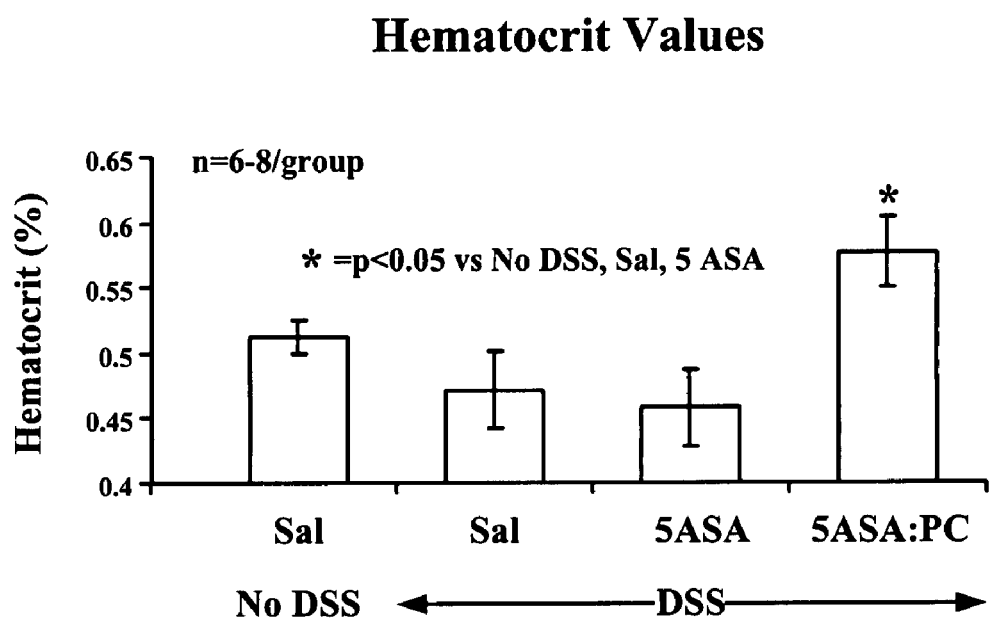
FIG. 17 depicts changes in hematocrit levels in Sprague Dawley male rats during a recovery period after DSS induced colitis for saline with no DSS in the drinking water and saline, 5ASA and a PC:5ASA formulation with DSS in the drinking water.

Referring now to FIG. 17, hematocrit data is shown. This measure of anemia due to GI bleeding was not significantly different among the experimental groups treated with DSS versus control (no DSS), but did tend to be lower in the DSS-treated groups except for those administered 5ASA:PC (Group 4), where it was significantly higher.

Figure 18:
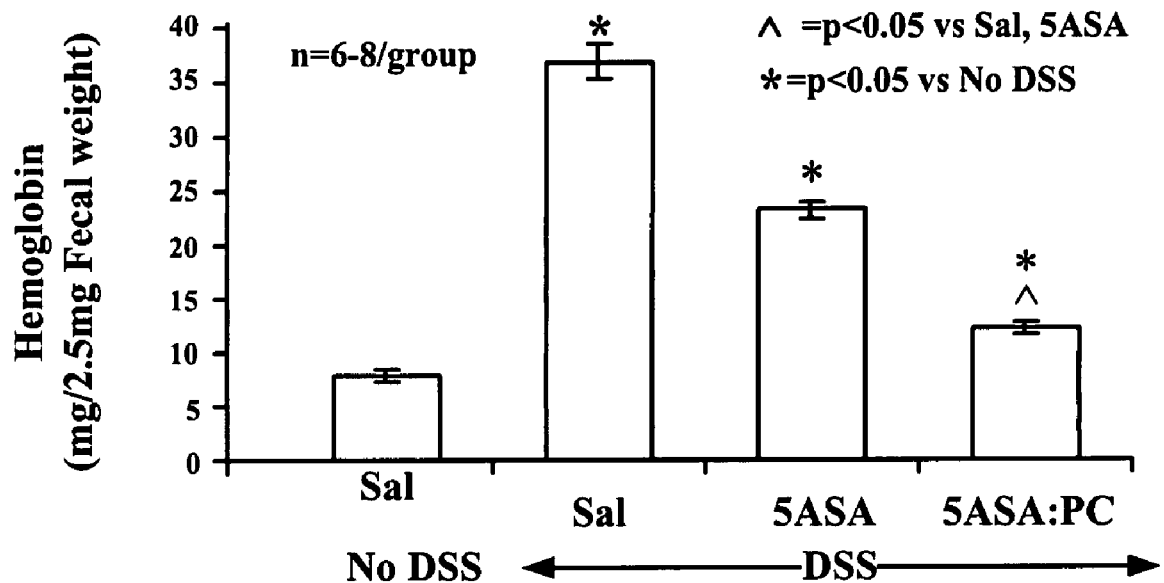
FIG. 18 depicts changes in fecal hemoglobin in Sprague Dawley male rats during a recovery period after DSS induced colitis for saline with no DSS in the drinking water and saline, 5ASA and a PC:5ASA formulation with DSS in the drinking water.

Referring now to FIG. 18, fecal hemoglobin data is shown. This direct measure of active GI bleeding demonstrated an increase in the saline-treated DSS group (Group 2) versus the control (no DSS) group (Group 1). This DSS-induced increase in GI fecal blood loss was partially reversed by 5ASA administration and completely reversed by 5ASA:PC administration. Significant differences ($p<0.05$) were observed between Group 4 versus Groups 2 & 3, but not Group 1.

DSS-induces colonic inflammation and bleeding in rats that is still evident 3 days post-DSS. 5ASA alone at a dose of 50 mg/kg administered twice daily intragastrically promotes tissue recovery from DSS-induced colitis and reduces GI bleeding. PC-5ASA when administered intragastrically at the same dose of active 5ASA induced full recovery of the mucosa from DSS-induced colitis with little or no evidence of GI bleeding.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

The invention claimed is:

1. A composition comprising 5-aminosalicylic acid (5ASA) and a phospholipid or a phospholipid-containing oil, wherein 5-aminosalicylic acid and said phospholipid are associated at a molecular level to form a complex.

2. The composition of claim 1, wherein the 5ASA treats symptoms of Inflammatory Bowel Disease (IBD) and the phospholipid enhances the activity of 5ASA.

3. The composition of claim 1, wherein a weight ratio of 5ASA to phospholipid or a phospholipid-containing oil is between about 1:10 and about 10:1.

4. The composition of claim 1, wherein the weight ratio of 5ASA to phospholipid or a phospholipid-containing oil is between about 1:5 and about 5:1.

5. The composition of claim 1, wherein the weight ratio of 5ASA to phospholipid or a phospholipid-containing oil is between about 2:1 and about 1:2.

6. The composition of claim 1, wherein the weight ratio of 5ASA to phospholipid or a phospholipid-containing oil is 1:1.

7. The composition of claim 1, wherein the composition is in the form of resin encapsulated microspheres capable of being released at pH values of 7 or higher.

8. The composition of claim 1, wherein 5ASA and the phospholipid are associated at a molecular level to form a complex.

9. The composition of claim 1, wherein 5ASA is covalently bonded to a reactive phospholipid via a diazo linkage.

10. The composition of claim 1, wherein the composition is in the form of resin encapsulated microspheres capable of being released at pH values of 7 or higher.

11. A method for treating Inflammatory Bowel Disease (IBD) comprising the step of:
   administering a composition comprising 5-aminosalicylic acid (5ASA) and a phospholipid to a patient having Inflammatory Bowel Disease (IBD).

12. The method of claim 11, wherein 5ASA treats symptoms of Inflammatory Bowel Disease (IBD) and the phospholipid enhances the activity of 5ASA.

13. The method of claim 11, wherein the administering step is an oral administering step, an enteral administering step or a rectal administering step.

14. The method of claim 13, wherein the administering step comprises a single administration, a periodic administration, an intermittent administration, or administration according to any administration protocol.

15. The method of claim 11, wherein a weight ratio of 5ASA to phospholipid or a phospholipid-containing oil is between about 1:10 and about 10:1.

16. The method of claim 11, wherein the weight ratio of 5ASA to phospholipid or a phosphotipid-containing oil is between about 1:5 and about 5:1.

17. The method of claim 11, wherein the weight ratio of 5ASA to phospholipid or a phospholipid-containing oil is between about 2:1 and about 1:2.

18. The method of claim 11, wherein the weight ratio of 5ASA to phospholipid or a phospholipid-containing oil is 1:1.

19. The method of claim 11, wherein the composition is in the form of resin encapsulated microspheres adapted to be released at pH values of 7 or higher.

20. The method of claim 11, wherein 5ASA and the phospholipid are associated at a molecular level to form a complex.

21. The method of claim 11, wherein 5ASA is covalently bonded to a reactive phospholipid via a diazo linkage.

* * * * *